United States Patent

Bellani

Patent Number: 5,703,233
Date of Patent: Dec. 30, 1997

[54] QUINILONE DISULFIDE AS INTERMEDIATES

[75] Inventor: Pietro Bellani, Rho, Italy

[73] Assignee: Archimica SpA, Orrigio, Italy

[21] Appl. No.: 494,353

[22] Filed: Jun. 26, 19951

Related U.S. Application Data

[63] Continuation of PCT/EP94/03513 filed Oct. 26, 1994.

[30] Foreign Application Priority Data

Oct. 27, 1993 [IT] Italy .................. MI94A2284

[51] Int. Cl.$^6$ .................. C07D 513/06; C07D 401/14
[52] U.S. Cl. .................. 544/32; 544/357
[58] Field of Search .................. 544/32

[56] References Cited

FOREIGN PATENT DOCUMENTS

| 165375 | 12/1985 | European Pat. Off. . |
| 522277 | 1/1993 | European Pat. Off. . |
| 2217710 | 11/1989 | United Kingdom . |

OTHER PUBLICATIONS

Synthetic Communications, 21(22), 2301–2308 (1991), Cecchetti, V. et al., "One–pot synthesis of Rufloxacin".

Primary Examiner—Mark L. Berch
Assistant Examiner—Bruck Kifle
Attorney, Agent, or Firm—Michael N. Meller

[57] ABSTRACT

A process for preparing rufloxacin using a compound of the formula I

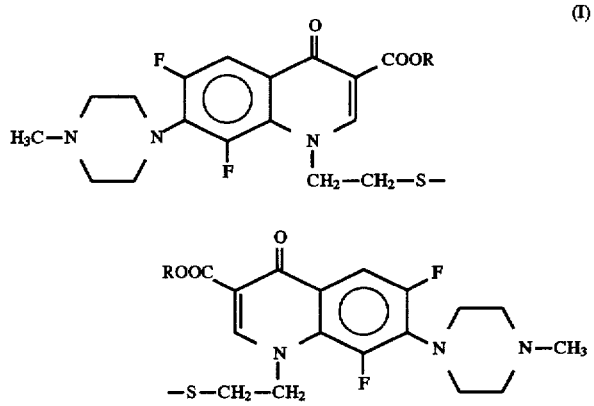

as a starting material is described, where R is herein defined.

3 Claims, No Drawings

QUINILONE DISULFIDE AS INTERMEDIATES

This application is a continuation of PCT/EP94/03513 filed Oct. 26, 1994.

The present invention concerns a new quinolone disulfide, a process for its preparation and the use thereof as intermediate in the synthesis of 9-fluoro-2,3-dihydro-10-(4-methylpiperazin-1-yl)-7-oxo-7H-pyrido [1,2,3-de][1,4] benzothiazin-6-carboxylic acid of formula (A)

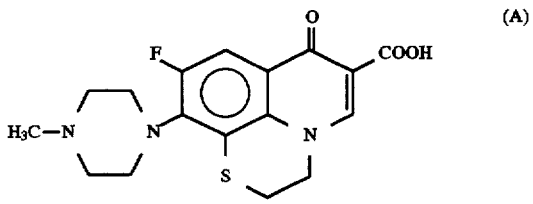

and of its pharmaceutically acceptable salts.

The compound of formula (A) is a new quinolone having a wide and powerful activity against Gram-positive and Gram-negative bacteria, a low toxicity as well as favorable pharmacokinetic. The compound is known under its International Non-proprietary Name of "rufloxacin", which will be used hereinbelow.

In clinical trials, rufloxacin is generally used in form of its hydrochloride and is described by V. Cecchetti et al. in J. Med. Chem. 1987, 30, 465–473 and in Synthetic Communications, 1991, 21(22) 2301–2308.

The first reported synthesis for the preparation of rufloxacin involves a great number of steps, at least ten, which provide all the construction of the tricyclic system of pyrido [1,2,3-de][1,4]benzothiazine and the introduction of 4-methylpiperazine, after the previous protection of the sulphur atom as sulfoxide. These processes involve, among other things, an oxidation at the sulphur atom of the benzothiazine and subsequent reduction to obtain the desired product in very small yields.

It has now been found that, starting from an alkyl 2,3,5-trifluoro-4-(4-methylpiperazin-1-yl) benzoylacetate, rufloxacin can be prepared in only three steps, through a new disulfide intermediate.

Thus, the present invention concerns, according to one of its aspects, a new quinolone disulfide having the formula (I)

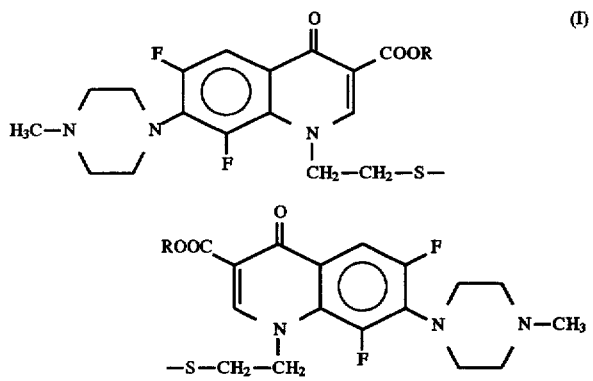

in which R represents a $C_1$–$C_4$ alkyl group, and its salts.

A quinolone disulfide of formula (I) wherein R is ethyl and its acid addition salts, particularly the hydrochloride, are preferred. The salts of the disulfide of formula (I) are the addition salts with inorganic acids such as hydrochloric, hydrobromic, sulfuric and phosphoric acid or with organic acids such as methanesulfonic, fumaric, maleic, oxalic and picric acid, the hydrochloride being the preferred.

The disulfide (I) is stable and can be easily stored for its use as an intermediate. By reduction, cyclization and hydrolysis, this compound is easily transformed into rufloxacin and its salts. The new compound having the formula (I) is easily prepared in one pot starting from an alkyl 2,3,5-trifluoro-4-(4-methylpiperazin-1-yl) benzoylacetate.

It is another object of the present invention to provide a process for the preparation of the disulfide having the formula (I) which comprises reacting an alkyl 2,3,5-trifluoro-4-(4-methylpiperazin-1-yl) benzoylacetate of formula (II)

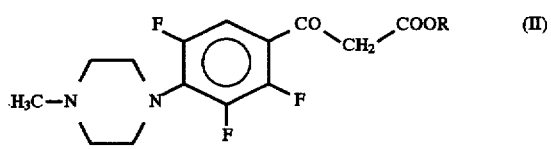

wherein R is as defined above, at first with an N,N-dimethylformamide dialkyl acetal of formula (III)

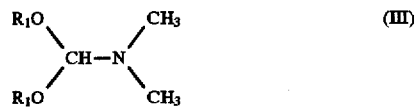

wherein $R_1$ is an alkyl of from 1 to 4 carbon atoms, in an organic solvent, then with 2-aminoethanethiol with concurrent cyclization in a basic medium and in the presence of air and isolating the quinolone disulfide (I) as such or in form of one of its salts.

The reaction of the ketoester (II) with the acetal (III) is carried out at a temperature of 80°+120° C. in an organic solvent, such as toluene at reflux. At the end of the reaction the solvent is totally or partially eliminated and the residue is immediately treated with 2-aminoethanethiol, preferably as a salt thereof such as the hydrochloride, in the presence of a base. This reaction is carried out in water, optionally in admixture with an organic solvent which may be the same as that of the precedent reaction, or even different, for example ethyl acetate or toluene. Cyclization takes place by treatment with a base at a temperature of 20+30° C. The base used may be organic, such as, for example, trimethylamine, triethyl amine or diazabicyclooctane, or inorganic, such as, for example, sodium or potassium hydroxide, sodium hydride, sodium or potassium acetate. The reaction is carried out in the presence of air. The formation of the disulfide is complete after a 10+15-hour stirring.

The quinolone disulfide (I) thus obtained may be isolated according to known methods, particularly by eliminating the salts, evaporating the solvent and taking up the residue with a solvent in which the product crystallizes, for example acetone. It may also be recrystallized from a mixture methanol/water (3:1 v/v).

The compound thus obtained of formula (I) may be isolated as a salt thereof or the raw free base may be transformed into one of its acid addition salts, for example with hydrochloric, hydrobromic, sulfuric, methanesulfonic, fumaric, maleic, oxalic acid.

The ketoester (II) used as starting material is known from the literature when R is ethyl and may anyway be prepared according to known methods (Chem. Pharm. Bull. 1986, 34, 4098–4102) from 2,3,4,5-tetrafluorobenzoic acid of formula (i)

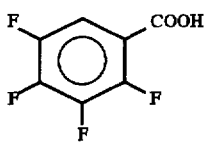

by reaction of its acid chloride (obtained with thionyl chloride in N,N-dimethylformamide) with a dialkyl malonate of formula

wherein R is as defined above, in the presence of a magnesium alchoholate, for example the ethylate, and by subsequent reaction of the compound (iii)

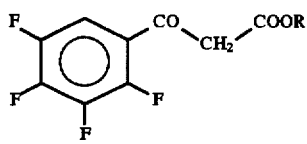

even without isolating it, with N-methylpiperazine. The new disulfide of formula (I) of the present invention is useful as intermediate in the preparation of rufloxacin.

Thus, the present invention concerns, according to another of its aspects, the use of a disulfide of formula (I), in which R is a $C_1$–$C_4$ alkyl group, for the synthesis of rufloxacin and its pharmaceutically acceptable salts.

For this purpose, the quinolone disulfide (I) is reduced to a thiol using a reducing agent such as sodium hydride, sodium metabisulfite or zinc in the presence of an acid with triphenyl phosphine in organic medium, in the presence of an acid, such as acetic acid or water.

At the end of the reduction, the cyclization is carried out according to the following scheme:

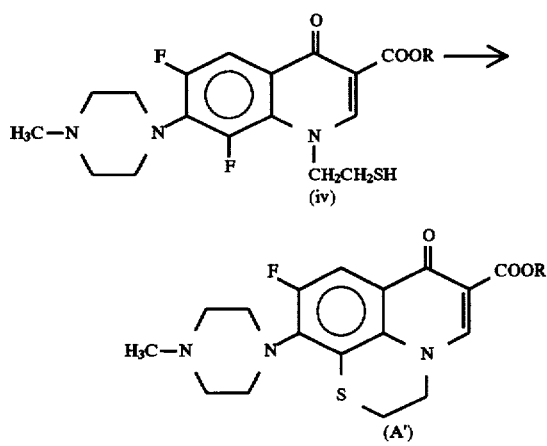

in which R is as defined above.

The cyclization (iv)→(A') is carried out by treatment with a base in an organic solvent, preferably ethyl acetate or N,N-dimethyl formamide. As a base potassium carbonate or sodium hydride are preferably employed. At the end the compound of formula (A') is subjected to a saponification with a base or in acetic acid with an inorganic acid to isolate rufloxacin in form of the corresponding inorganic salt. Using hydrochloric acid rufloxacin hydrochloride for pharmaceutical use is directly obtained and such a procedure is particularly preferred.

The following examples illustrate the invention without, however, limiting it.

EXAMPLE 1

A mixture of 80 g (0.232 m) of ethyl 2,3,5-trifluoro-4-(4-methyl piperazin-1-yl)benzoylacetate (II, R=$CH_2H_5$) and 45 g (0.377 m) of N,N-dimethylformamide dimethyl acetal (III, $R_1$=$CH_3$) in 250 ml of toluene is heated at reflux, then the solvent is distilled off to reach 110° C. and a further amount of toluene is added thereinto to about the initial volume. The solution thus obtained is washed twice with water, then 40 ml of water and 30 g of 2-aminoethanethiol hydrochloride (0.388 m) are added thereinto and 25 ml of 30% sodium hydroxide are added dropwise, in 30 minutes, to the reaction mixture. Such a mixture is stirred 2 hours at room temperature (20°+30° C.) then the aqueous phase is eliminated and the organic phase is washed with water, dried and concentrated under vacuum to dryness. The residue is taken up with 700 ml of ethyl acetate and 50 g of micronized potassium carbonate are added to the solution. The mixture is stirred for 15 hours in the presence of air, then it is heated 2 hours at reflux. After having filtered the salts off, the solution is concentrated under vacuum, the residue is taken up with ethyl acetate and filtered. Thus, 80 g of bis-[2-[((6, 8-difluoro-3-ethoxycarbonyl-4-oxo-7-(4-methylpiperazin-1-yl) -1,4-dihydroquinolin-1-yl]]ethyldisulfide (I, R=$C_2H_5$) are obtained.

$^1$H-NMR (300 mHz, $CDCl_3$): 1.41 (t, 3H, $\underline{CH_3}$—$CH_2$, J=7 cps); 2.36 (s, 3H, N—$CH_3$); 2.56 (m, 4H, piperazine); 3.10 (t, 2H, $CH_2$—S); 3.36 (m, 4H, piperazine); 4.39 (q, 2H, $CH_3$—$\underline{CH_2}$, J=7 cps); 4.51 (m, 2H, $CH_2$—N); 7.97 (dd, 1H, aromatic, $J_{HF}$=2 cps, 12 cps); 8.34 (s, 1H, =CH).

EXAMPLE 2

A mixture of 60 g of ethyl 2,3,5-trifluoro-4-(4-methylpiperazin-1-yl) benozylacetate, 35 ml of N,N-dimethylformamide dimethyl acetal and 220 ml of toluene is heated at reflux for 1 hour. The solvent is distilled off an a further volume of toluene is added. The solution is cooled to 20° C., washed with water and successively 60 ml of water, 23 g of 2-aminoethanethiol hydrochloride and 31 g of sodium acetate trihydrate are added. After stirring 2 hours at room temperature the organic phase is separated, washed with water, dried and concentrated under vacuum to dryness. The residue is treated with 600 ml of acetonitrile and 60 g of micronized anhydrous potassium carbonate are added. The suspension is stirred for 10 hours in the presence of air, then heated for 90 minutes at reflux. After filtration of the salts, the solution is concentrated under vacuum to dryness. The residue is treated with water and filtered to give 58.8 g of quinolone disulfide (I, R=$C_2H_5$).

EXAMPLE 3

A mixture of 40 g of ethyl 2,3,5-trifluoro-4-(4-methylpiperazin-1-yl) benzoylacetate, 22.5 g of N,N-dimethylformamide dimethyl acetal and 125 ml of toluene is heated at reflux for 2 hours. The solvent is distilled off and a further volume of toluene is added. To the solution thus obtained 20 ml of water and 22 g of 2-aminoethanethiol hydrochloride are added thereinto, and successively in 1 hour 32 ml of 30% sodium hydroxide. After stirring 2 hours at room temperature, the organic phase is separated, washed with water, dried and concentrated under vacuum to dryness. The residue is extracted with 280 ml of ethyl acetate and treated with 27.5 g of micronized potassium carbonate. The suspension is stirred for 15 hours in the presence of air, then heated 2 hours at reflux. After filtration of the salts, the solution is concentrated under vacuum and the residue is crystallized from ethyl acetate to give 45.7 g of quinolone disulfide (I, R=$C_2H_5$). Yield: 96%.

EXAMPLE 4

A mixture of 52.8 g of ethyl 2,3,5-trifluoro-4-(4-methylpiperzin-1-yl) benzoylacetate, 20 g of N,N-dimethylformamide dimethyl acetal and 165 ml of N,N-dimethylformamide is heated at 100°–105° C. for 1 hour. To the solution 26 ml of water, 18.7 g of 2-aminoethanethiol hydrochloride are added thereinto and successively, in 30 minutes, 32.8 ml of 30% sodium hydroxide. The reaction mixture is stirred for 1 hour at 20°+25° C., then poured into 450 ml ice-water and extracted with 350 ml of ethyl acetate. The organic phase is washed with water, dried and treated with 33 g of potassium carbonate. The suspension is stirred in the presence of air for 20 hours. After filtration, the solution is concentrated under vacuum to a small volume. The crystalline product is filtered and 55.7 g of quinolone disulfide (I, R=$C_2H_5$) are obtained. Yield: 88.6%.

EXAMPLE 5

A mixture of 40 g of ethyl 2,3,5-trifluoro-4-(4-methylpiperazin-1-yl) benzoylacetate, 22.5 g of N,N-dimethylformamide dimethyl acetal and 125 ml of benzene is heated at reflux for 2 hours. The solvent is distilled off and a further volume of benzene is added. To the solution thus obtained 20 ml of water and 22 g of 2-aminoethanethiol hydrochloride are added thereinto, and successively in 1 hour 32 ml of 30% sodium hydroxide. After stirring 2 hours at room temperature the organic phase is separated, washed with water, dried and concentrated under vacuum to dryness. The residue is extracted with 280 ml of ethyl acetate and treated with 27.5 g of micronized potassium carbonate. The suspension is stirred for 15 hours in the presence of air, then heated 2 hours at reflux. After filtration of the salts, the solution is concentrated under vacuum and the residue is crystallized from ethyl acetate to give 45.7 g of quinolone disulfide (I, R=$C_2H_5$). Yield: 96%.

EXAMPLE 6

Preparation of a quinolone disulfide (I, R=$C_2H_5$) starting from 2,3,4,5-tetrafluorobenzoic acid (a) Ethyl 2,3,5-trifluoro-4-(4-methylpiperzin-1-yl) benzoylacetate (II, R=$C_2H_5$).

A suspension of 200 g of 2,3,4,5-tetrafluorobenzoic acid, 225 ml of thionyl chloride and 5 ml of N,N-dimethylformamide is heated at reflux for 3 hours. After cooling at 40° C. the thionyl chloride in excess is evaporated off under vacuum. The residue is taken up with toluene and the solution is concentrated again at 40° C. under vacuum. Thus 219 g of raw 2,3,4,5-tetrafluorobenzoyl chloride are obtained as a yellowish oil. A mixture of 1200 ml of toluene, 220 g of diethyl malonate and 153 g of magnesium ethylate, prepared at 20° C., is heated one hour at reflux, then it is cooled to 5° C. and the acid chloride above obtained is added thereto, by keeping the temperature less than 10° C. After a 3-minutes stirring, the mixture is made acid with concentrated hydrochloride acid and the two phases are separated. The organic phase is diluted with water, made acid with sulfuric acid to pH 1.0 and heated at reflux for 7 hours, namely until the reaction is over. The mixture is cooled, the aqueous phase is separated and the organic one is taken up with water and made basic with sodium hydroxide to a very basic pH value (13+14). The aqueous phase is separated and the organic one is extracted again with water. The combined aqueous phases are made acid with concentrated hydrochloric acid to pH 1 and extracted twice with toluene. The toluene phase is concentrated under vacuum, the residue is taken up with 1250 ml of acetonitrile. To this mixture, at first 80 g of sodium bicarbonate and then 110 ml of N-methylpiperazine are added and the reaction mixture is heated 3 hours at reflux. By dilution with water the desired product precipitates and it is then filtered and washed with water. The wet product thus obtained is suspended in toluene and the suspension is evaporated by distillation until the solution becomes anhydrous. This solution contains 0.89 moles of ethyl 2,3,5-trifluoro-4-(4-methylpiperazin-1-yl) benzoylacetate and is directly used for the subsequent step (b).

(b) To the toluene solution of ethyl 2,3,5-trifluoro-4-(4-piperazin-1-yl)benzoylacetate (II, R=$C_2H_5$) previously obtained, 173 ml of N,N-dimethylformamide dimethyl acetal (III, $R_1$=$CH_3$) are added, then the solution is treated as described in Example 1 to obtain 333.4 of quinolone disulfide. The global yield starting from 2,3,4,5-tetrafluorobenzoic acid is 78.8%.

EXAMPLE 7

Preparation of rufloxacin hydrochloride starting from a quinolone disulfide (I, R=$C_2H_5$)

(a) To a suspension of 0.8 g of sodium hydride (60% in oil) in 10 ml of N,N-dimethylformamide is slowly added a solution of 8.2 g (0.02 m) of quinolone disulfide (I, R=$CH_2H_5$) in 40 ml of N,N-dimethyl formamide. The reaction mixture is stirred at room temperature for 1 hour, treated with a mixture of methanol/water/acetic acid (1:1:1 v/v/v) and then poured into 50 ml of ice-water. The crystalline product is collected by filtration, washed with water and acetone to give 7.75 g of rufloxacin ethyl ester.

(b) A solution of 10 g of rufloxacin ethyl ester into 30 ml of acetic acid and 10 ml of 35% hydrochloric acid is refluxed for 2 hours. To the collected solution 135 ml of acetone are added and the separated product is collected by filtration. The wet residue is suspended in a mixture ethanol/water, heated at 55°+60° C. for 15 minutes and filtered. Thus 9.8 g of pure rufloxacin hydrochloride are obtained.

I claim:

1. A process of preparing rufloxacin, a compound of formula (A)

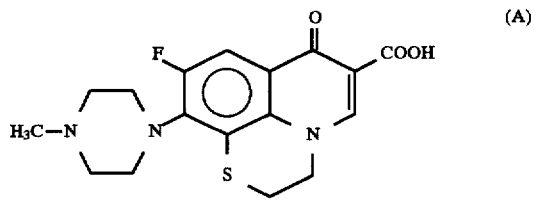

and its pharmaceutically acceptable salts, in which is used a quinolone disulfide of the formula (I)

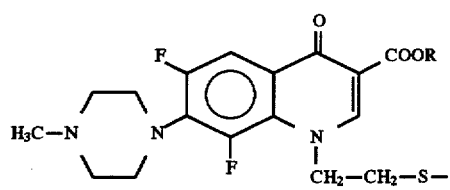
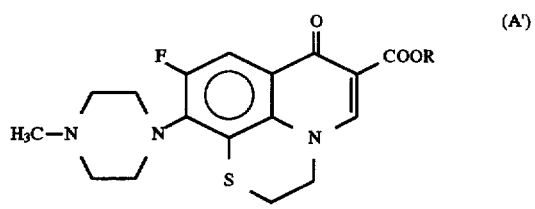
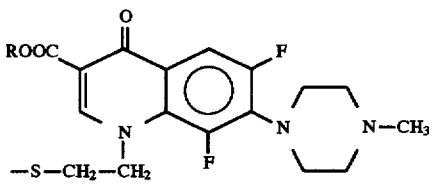

wherein R represents a $C_1$–$C_4$-alkyl group, and its salts which comprises reducing a compound of formula (I) with a suitable reducing agent and cyclyzing the resultant compound with a base to afford a compound of Formula (A')

and then hydrolyzing a compound of formula A' to afford a compound of formula (A) and, if required, preparing its pharmaceutically acceptable salts.

2. A process according to claim 1 wherein in Formula I, R is ethyl and its acid addition salts.

3. A process according to claim 2 wherein the acid addition salt is the dihydrochloride.

* * * * *